(12) United States Patent
Ratner

(10) Patent No.: US 6,502,573 B1
(45) Date of Patent: Jan. 7, 2003

(54) PORTABLE SINGLE PATIENT USE CARBON DIOXIDE DETECTOR

(75) Inventor: Jeffrey B. Ratner, Pinellas Park, FL (US)

(73) Assignee: Mercury Enterprises, Inc., Clearwater, FL (US)

( * ) Notice: Subject to any disclaimer, the term of this patent is extended or adjusted under 35 U.S.C. 154(b) by 0 days.

(21) Appl. No.: 10/001,487

(22) Filed: Nov. 15, 2001

(51) Int. Cl.[7] .............................................. A61M 16/00
(52) U.S. Cl. ............................ 128/207.17; 128/202.22; 128/205.23
(58) Field of Search ........................ 128/205.27, 205.28, 128/201.25, 202.22, 202.28, 202.29, 204.22, 205.23, 207.14, 207.15; 600/532, 353

(56) References Cited

U.S. PATENT DOCUMENTS

| | | | |
|---|---|---|---|
| 4,205,043 A | * 5/1980 | Esch et al. ..................... 422/56 |
| 4,879,999 A | * 11/1989 | Leiman et al. ......... 128/207.14 |
| 5,005,572 A | 4/1991 | Raemer et al. |
| 5,197,464 A | 3/1993 | Babb et al. |
| 5,273,029 A | * 12/1993 | Wilk et al. ............. 128/200.26 |
| 5,291,879 A | 3/1994 | Babb et al. |
| 5,375,592 A | * 12/1994 | Kirk et al. ............. 128/207.14 |
| 5,468,451 A | 11/1995 | Gedeon |
| 5,765,550 A | * 6/1998 | Psaros et al. .......... 128/202.27 |
| 5,846,836 A | 12/1998 | Mallow |
| 5,965,061 A | 10/1999 | Larsson et al. |
| 6,144,869 A | * 11/2000 | Berner et al. ................ 600/347 |
| 6,187,596 B1 | * 2/2001 | Dallas et al. ................ 436/169 |
| 6,378,522 B1 | * 4/2002 | Pagan .................... 128/207.14 |

* cited by examiner

Primary Examiner—Glenn K. Dawson
Assistant Examiner—Michael Mendoza
(74) Attorney, Agent, or Firm—Larson & Larson, PA; James E. Larson

(57) ABSTRACT

The $CO_2$ detector has a bottom housing attached to a top housing. The bottom housing contains a rotatable port engageable to an intubation tube and multiple parallel integral filter support ridges on a top surface of a floor. A filter pad overlies the integral filter support ridges and a baffle overlies the filter pad. The baffle has multiple parallel filter support ridges on a bottom surface cooperating with the filter support ridges integral with the bottom housing to maintain the filter pad in position. The baffle has an air flow guide on a top surface and air passages. The top housing has a port connected to a CPR bag and a clear plastic disc overlying a $CO_2$ calorimetric indicator paper. The colorimetric indicator paper is shown through a clear plastic cover after removing backing on the indicator paper through a sealable slot.

15 Claims, 8 Drawing Sheets

PORTABLE SINGLE PATIENT USE CARBON DIOXIDE DETECTOR

FIELD OF THE INVENTION

This invention relates to carbon dioxide ($CO_2$) detectors. More particularly, it refers to a device containing $CO_2$ calorimetric indicator paper, the device attached to an endotracheal tube for detecting $CO_2$ levels in the breath of a patient following intubation.

BACKGROUND OF THE INVENTION

U.S. Pat. No. 4,691,701 describes an early portable $CO_2$ detector in the form of a transparent disc containing a chemical substance exhibiting a color change indication when exposed to carbon dioxide from a patient.

U.S. Pat. Nos. 5,197,464 and 5,291,879 describe methods of monitoring $CO_2$ levels in a patient using a reversible indicator solution so that the indicator changes color continuously with the breathing of a patient.

Other references that include references to $CO_2$ color change devices are U.S. Pat. Nos. 4,790,327; 4,928,687; 4,994,117; 5,005,572; 5,166,075; 5,179,002; 5,846,836 and 5,965,061.

A critical step in the intubation of a patient is a determination that the breathing tube or intubation tube or endotracheal tube is placed in the trachea and not in the esophagus. If the tube is in the esophagus, there is no return of $CO_2$ from a patient's breath. If the tube is in the trachea, $CO_2$ will be present up to about five percent concentration. Since it is common in emergency situations for less highly skilled technicians to apply endotracheal tubes attached to a cardiopulmonary resuscitator (CPR) to a patient's airway, it is important to have a portable single patient breathing apparatus such as a CPR containing a device confirming the proper initial placement and continuous placement of the endotracheal tube. A $CO_2$ detector communicating with a CPR bag apparatus serves this purpose. Although such detector's exist, alternate detectors which provide ease of use, low cost and connection to existing CPR apparatus is needed.

SUMMARY OF THE INVENTION

The invention described herein is an improvement over prior $CO_2$ detectors used with CPR bags to ventilate patients. This $CO_2$ detector has an easily mountable colorimetric indicator paper that continues to change color over several days in response to a patient's exhaled breath. It is easily mountable in communication with a CPR bag, is lightweight and gives easily readable and reliable $CO_2$ detection.

The inventive $CO_2$ detector has a top housing integral with an inhale/exhale port. This port is connected to a CPR bag. A clear plastic disc is mounted to the top housing. The clear plastic disc is integral with a disc support containing snap legs engageable to complimentary grooves on the circumference of a bore through the top housing. Indicator paper is mounted on the inside surface of the plastic disc. Backing paper on the indicator paper is removed by pulling on the backing paper protruding from a slot below the disc. A bottom housing is glued or heat welded to the housing cover after a filter and baffle are mounted between the top housing and the bottom housing containing a downwardly directed port. This bottom housing port is connected to an intubation tube leading to a patient's trachea. Provided the tube is properly placed, the breath of the patient will cause a color change on the calorimetric indicator paper viewed through the clear plastic cover of the $CO_2$ detector of this invention.

BRIEF DESCRIPTION OF THE DRAWINGS

The invention can be best understood by those having ordinary skill in the art of patient intubation by following the detailed description when considered in conjunction with the accompanying drawings in which.

DETAILED DESCRIPTION OF THE INVENTION

Figure 1:
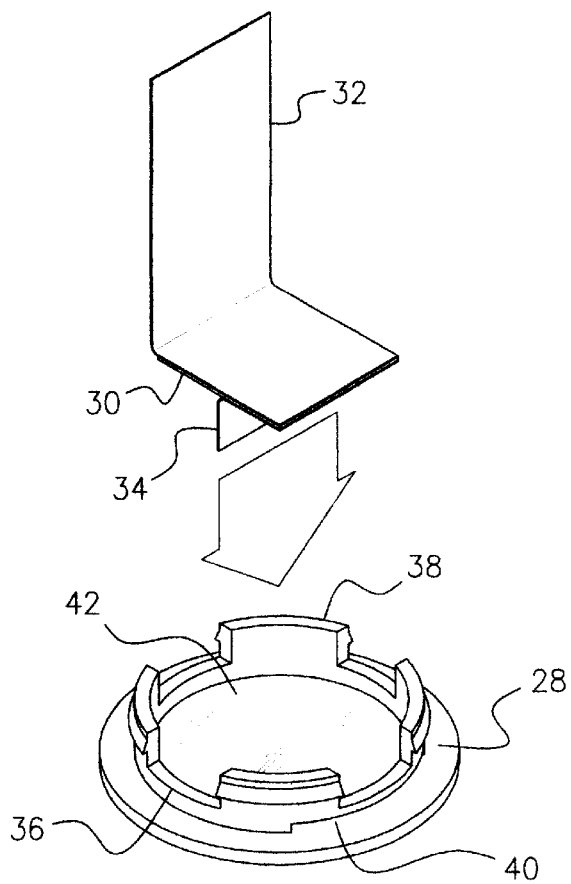
FIG. 1 is an exploded view in perspective of the indicator paper being affixed to a bottom surface of a disc for the $CO_2$ detector of the invention.

Throughout the following detailed description, the same reference numerals refer to the same elements in all figures.

Figure 6:
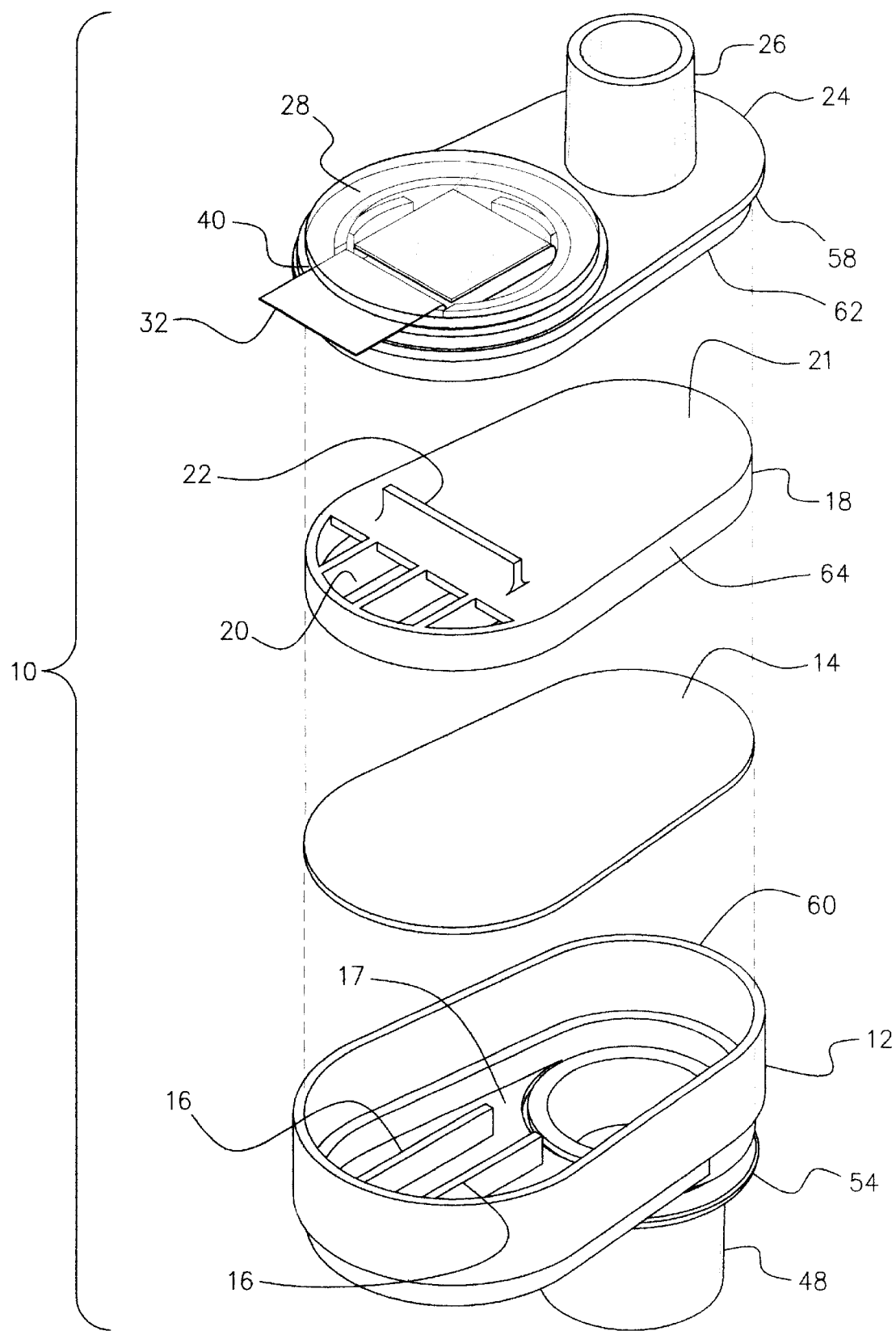
FIG. 6 is an exploded view of components of the $CO_2$ detector.
Figure 8:
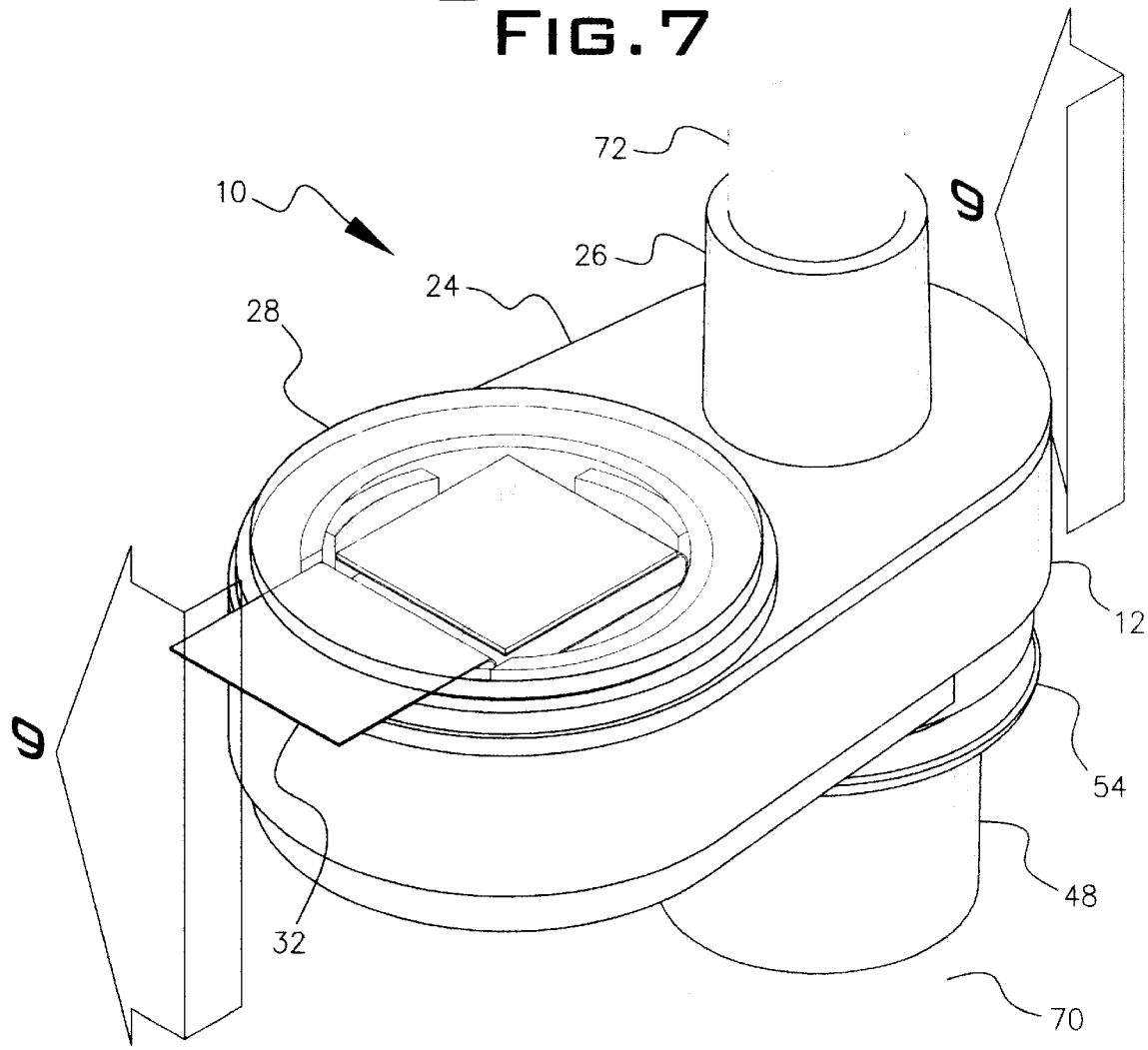
FIG. 8 is a perspective view of the $CO_2$ detector.

The $CO_2$ detector 10 of this invention shown in FIG. 8 has several principal components as shown in FIG. 6. The detector 10 has a bottom housing 12, a filter 14 resting on ridges 16 integral with a top surface of a floor 17 of the bottom housing 12. On top of filter 14 is a baffle 18 containing multiple air holes 20 and an air flow guide 22 on a top surface 21 of baffle 18. A top housing 24 contains an integral inhale/exhale port 26. Also attached to the top housing 24 is a clear plastic disc 28 overlaying a calorimetric indicator paper covered by backing paper 32.

Figure 2:
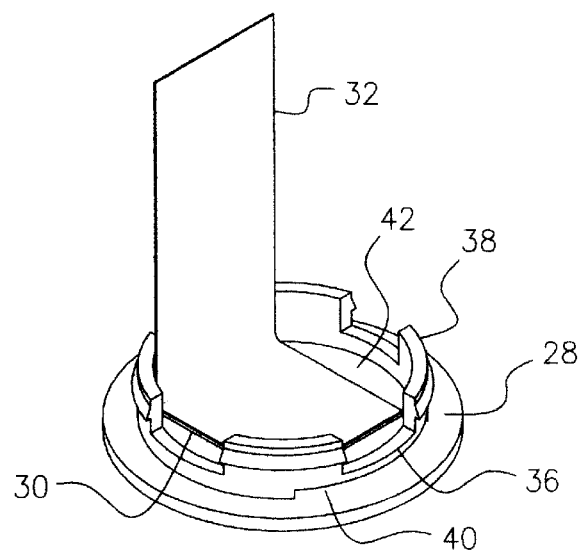
FIG. 2 is a perspective view of the indicator paper backing prior to insertion in a slot on a disc support.
Figure 3:
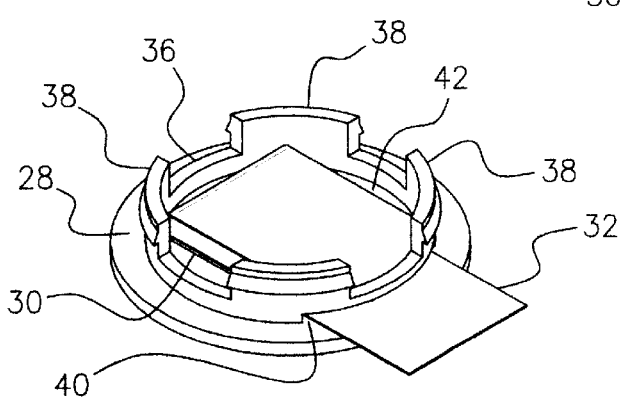
FIG. 3 is a perspective view of the indicator paper backing inserted into the slot on the disc support.

Referring to FIGS. 1–3, the $CO_2$ calorimetric indicator paper 30, employed in this invention, is affixed to a bottom surface 42 of disc 28. Disc 28 is integral with a disc support 36. The disc support 36 has multiple snap legs 38 and a slot 40 for receiving and subsequently removing a backing paper 32. The colorimetric $CO_2$ indicator paper 30 comes covered on a top surface by the paper backing 32 and on a bottom surface by a paper backing 34. Initially, the paper backing 34 is removed so that an adhesive on the bottom surface of the colorimetric $CO_2$ indicator paper 30 can be stuck to a bottom surface 42 of disc 28. As seen in FIG. 2, the paper backing 32 is folded down and passed through slot 40 as shown in FIG. 3. When the indicator paper is ready for use, the paper backing 32 protruding from slot 40 is pulled out to expose the bottom surface of the indicator paper 30.

Figure 4:
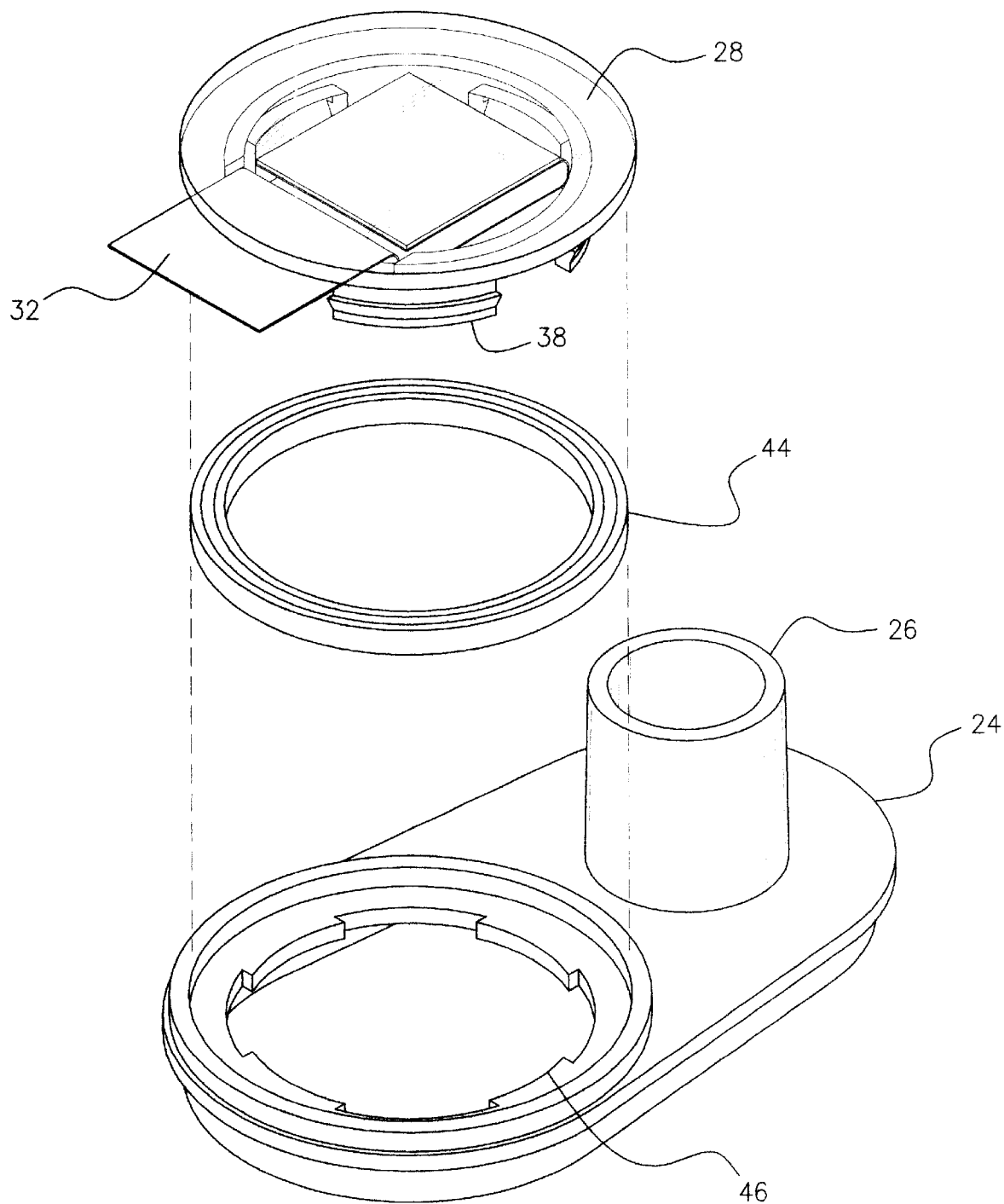
FIG. 4 is an exploded view in perspective of the components in the top housing of the $CO_2$ detector.

As seen in FIG. 4, the clear plastic disc 28 loaded with the indicator paper and its backing paper 32 is engaged over a disc support lock 46 in top housing cover 24. The pliable sealing ring 44 is interposed between the disc 28 outer edge and the outer edge of the disc support lock 46. Sealing ring 44 seals slot 40 after the backing paper 32 is pulled out to expose indicator paper 30.

Figure 5:
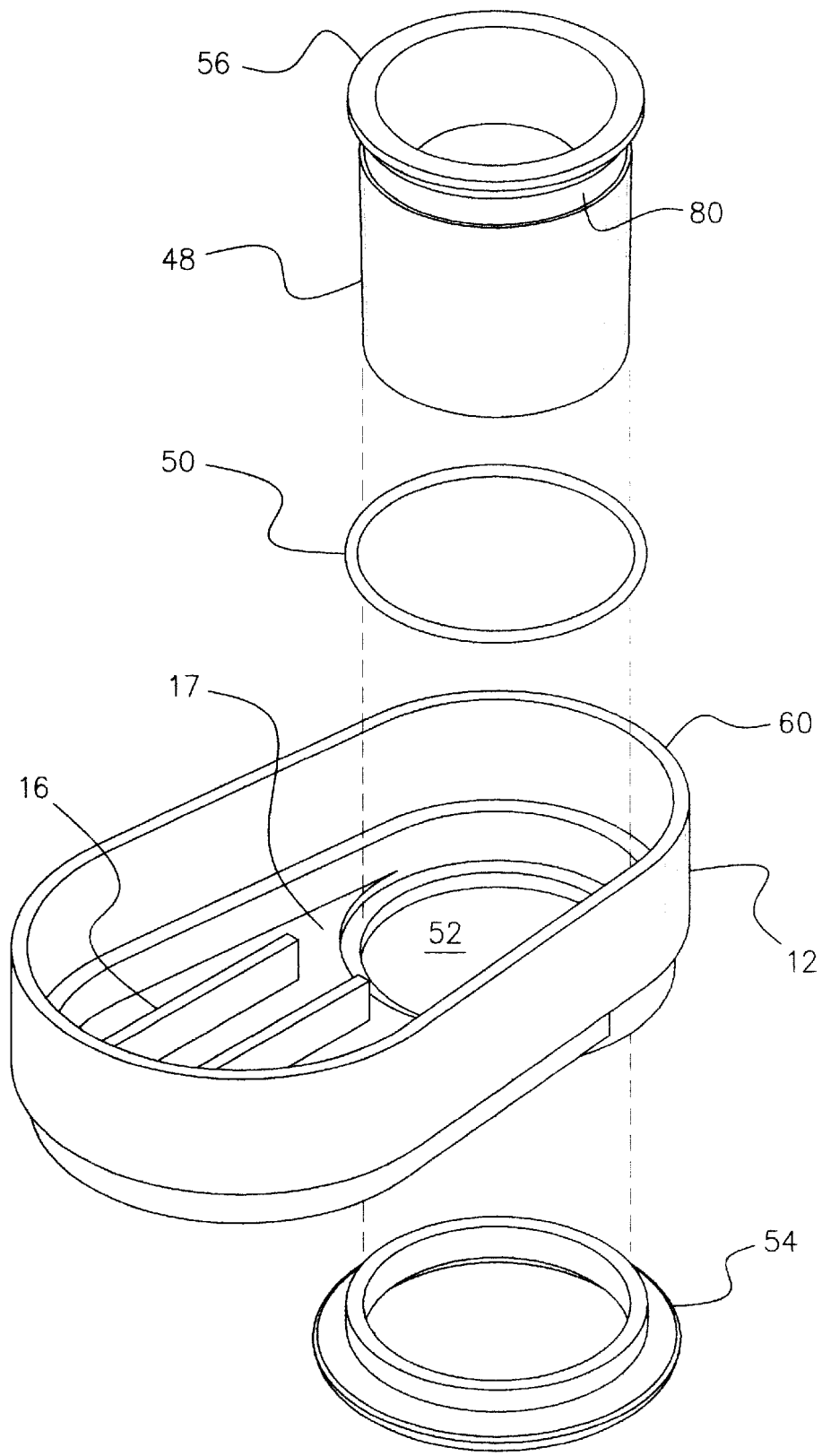
FIG. 5 is an exploded view in perspective of the components included in the bottom housing of the $CO_2$ detector.
Figure 7:
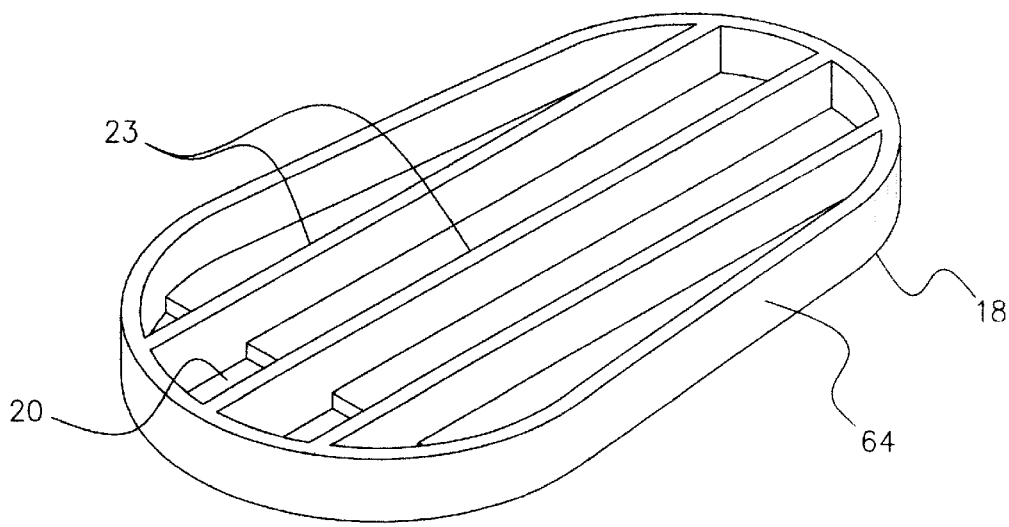
FIG. 7 is a bottom plan view of the baffle shown in FIG. 6.

The $CO_2$ detector is assembled as shown in FIGS. 5–6. The bottom housing 12 contains an aperture 52 and ridges 16. An O-ring 50 is placed around the edge of aperture 52 and a port 48 is then dropped in above the O-ring so that top annular edge 56 of the port 48 rests on the O-ring 50. A retaining ring 54 snaps into groove 80 in the port 48 as the port 48 seats in aperture 52. The filter 14 is then laid over the ridges 16. Ridges 23 shown in FIG. 7, on the bottom surface 25 of the baffle 18 is placed over filter 14. The top housing 24 containing the inhale/exhale port 26 and the clear plastic disc 28 is then snap fit, glued or heat welded along edge 58 to surface 60 on the bottom housing. Ridges 16 on the bottom housing floor 17 and ridges 23 from the bottom surface 25 of baffle 18 hold the filter 14 in position.

Figure 9:
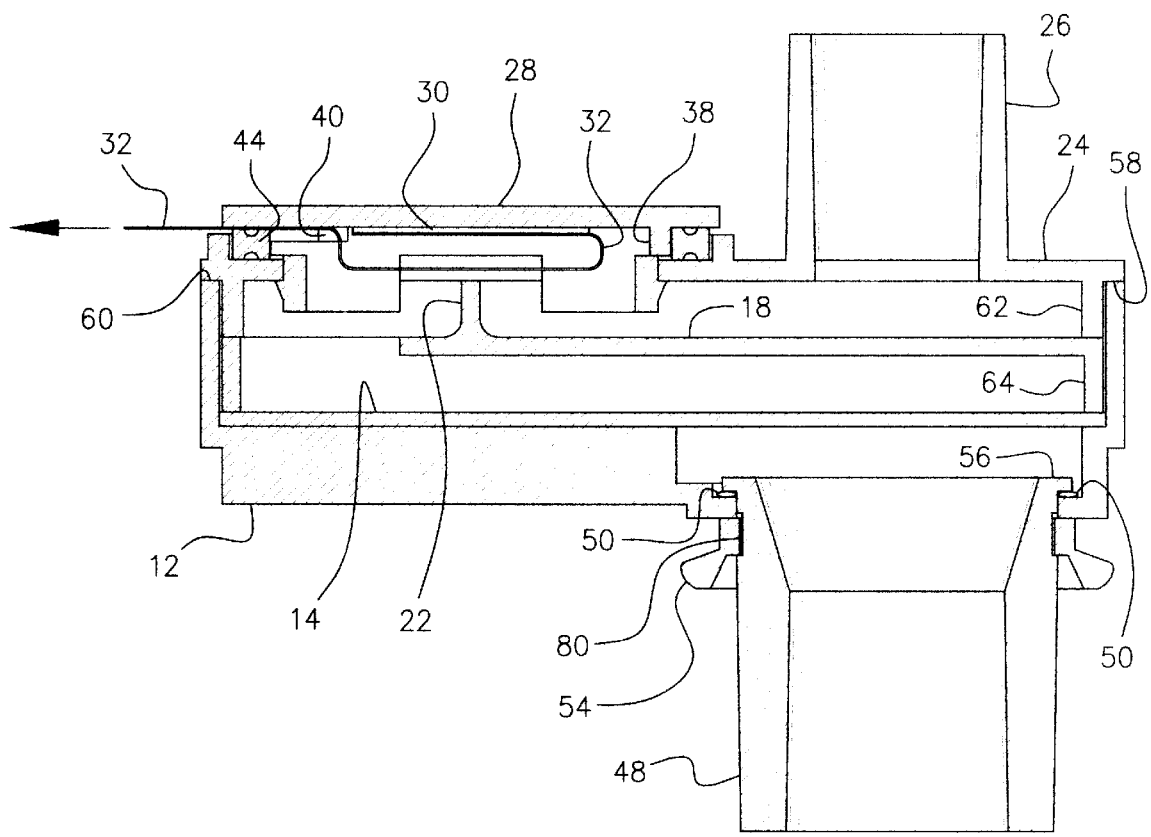
FIG. 9 is an elevational view in section of the $CO_2$ detector of FIG. 8 along line 9—9.

As shown in FIG. 9, the top housing 24 has a skirt 62 that rests on the top surface of baffle 18 and a skirt 64 on baffle 18 rests on the filter 14.

Figure 10:
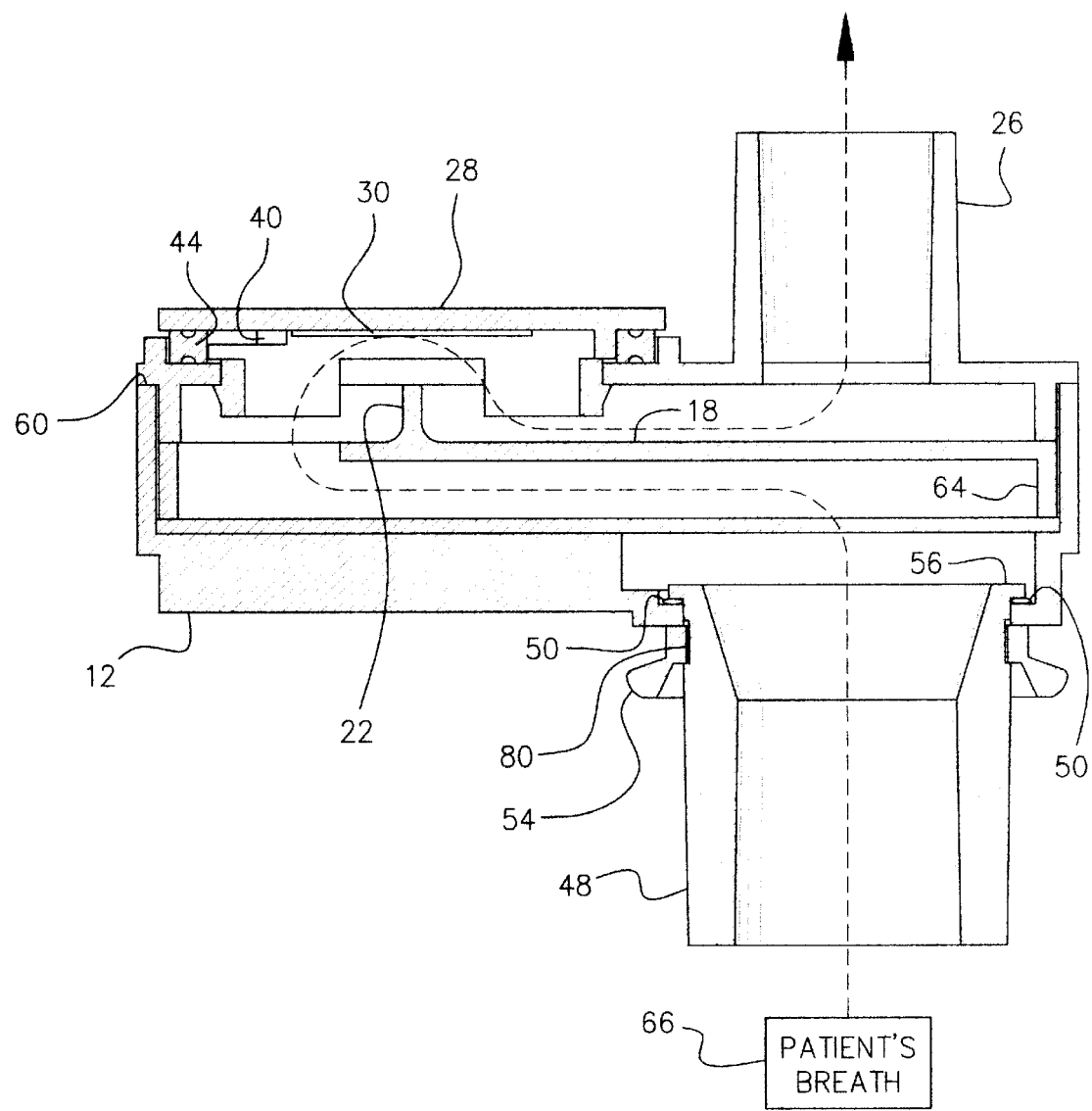
FIG. 10 is an elevational view in section showing the route of a patient's breath through the $CO_2$ detector.
Figure 11:
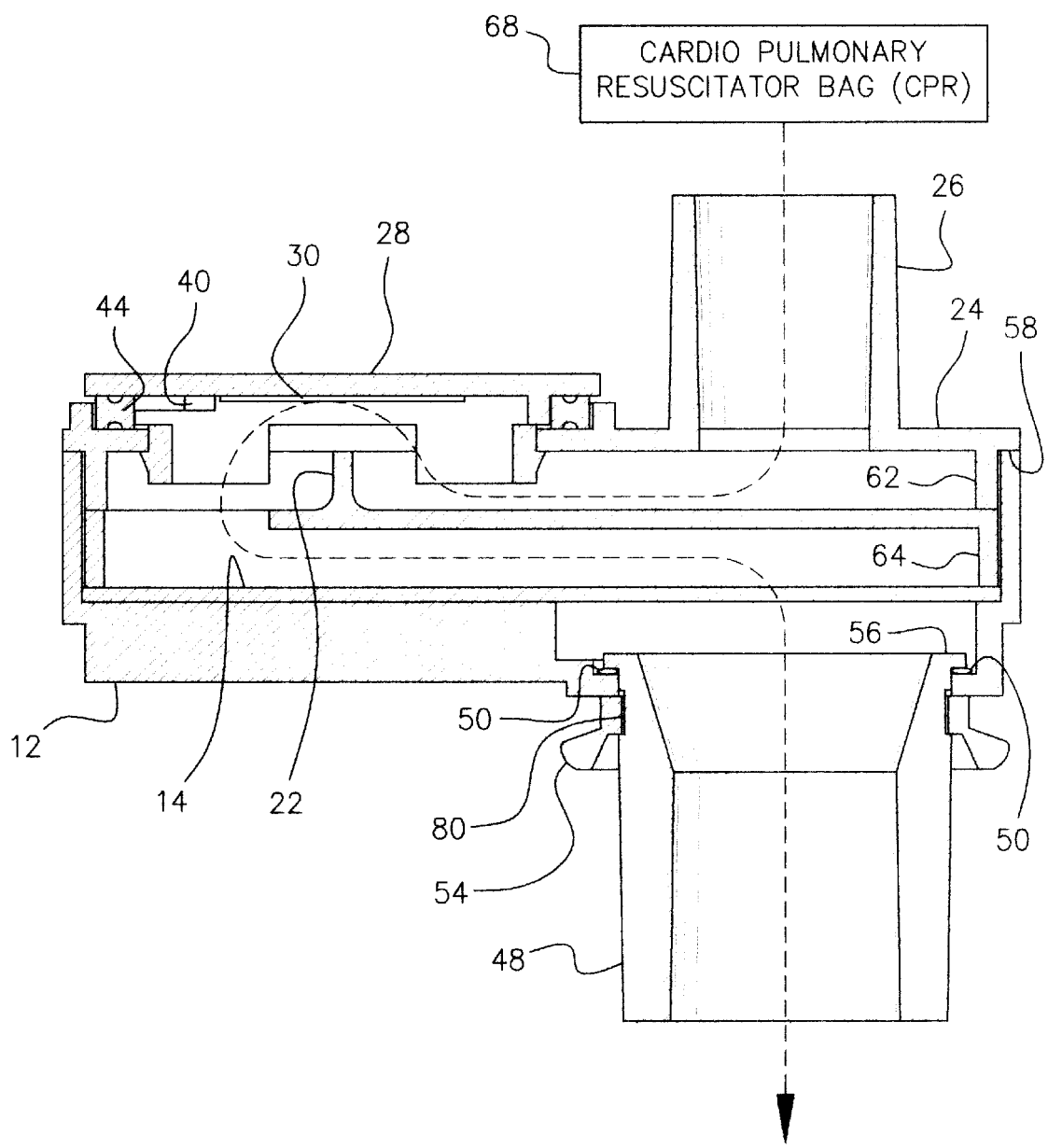
FIG. 11 is an elevational view in section showing the route of air flow from a CPR bag going to the patient through the $CO_2$ detector.

As shown in FIGS. 8 and 10, the rotatable port 48 which is attached to an intubation tube 70 leads to a patient's trachea, not shown. As the patient breathes out, $CO_2$ gas is expelled as shown in FIG. 10 through the port 48 and through the $CO_2$ detector 10. As the air passes by the calorimetric indicator paper 30, it causes the paper to change color indicating-that up to five percent of the breath contains $CO_2$. The breath passes out through port 26 and through a CPR bag patient port 72. When the CPR apparatus 68 expels air or oxygen, the air or oxygen passes down as shown in FIG. 11 through the port 26, passes by the indicator paper 30 to change its color once again, with the air or oxygen then passing out through port 48 and then through an intubation tube 70 to the patient's trachea. If the intubation tube 70 is not located in the trachea but has been improperly placed or ends up some how in the esophagus then the patient's breath, as shown in FIG. 10, will not contain higher than ambient $CO_2$ and will not change the color of the indicator paper 30. This is an indication that the intubation tube 70 is in the wrong position in the patient's body and should be immediately changed to place it properly into the trachea.

The components of the invention are made of plastic with the disc made of clear plastic. The remaining components may or may not be made out of the clear plastic. The filter paper is commercial grade obtained from 3M Corporation identified as FILTRETE®. The indicator paper backing 32 and 34 can be any acceptable commercial grade backing paper with a calorimetric indicator 30 such as described in U.S. Pat. Nos. 5,005,572 and 5,965,061, incorporated herein by reference.

The above description has described specific structural details of the $CO_2$ detector of this invention. However, it will be within one having ordinary skill in the art to make modifications without departing from the spirit and scope of the underlying invention's inventive concept. The inventive concept is not limited to the structure described, but includes such modifications as would be considered equivalent.

Having thus described the invention, what is claimed and desired to be secured by letters patent is:

1. A carbon dioxide ($CO_2$) detector for use with a cardiopulmonary resuscitator (CPR) device, the $CO_2$ detector comprising:

a top housing containing an inhale/exhale port connected to a CPR device, the top housing having a bore for receipt of a support for a clear plastic disc overlaying a chemically treated calorimetric indicator paper;

the indicator paper being partially covered with a backing paper prior to use, the backing paper protruding through a slot in the support and being removed by pulling on the protruding backing paper to fully expose the indicator paper;

a sealing ring juxtaposed to a bottom outer surface of the disc to seal the slot after removal of the backing paper; and a bottom housing attached to the top housing, the bottom housing having a port for connection by a tube to a patient's trachea.

2. The $CO_2$ detector according to claim 1 wherein the a bottom housing port is engageable to an intubation tube, the bottom housing enclosing integral multiple filter support ridges, a filter pad overlying the filter support ridges and a baffle overlying the filter pad, the baffle having multiple filter support ridges on a bottom surface cooperating with the filter support ridges integral with the bottom housing to maintain the filter pad in position.

3. The $CO_2$ detector according to claim 1 wherein the top housing bore is an opening proximal to the inhale/exhale port, an inner circumference of the opening containing locking slots, for receipt of multiple snap legs downwardly directed from the support, the snap legs engaging and locking to the locking slots to retain the disc on the top housing.

4. The $CO_2$ detector according to claim 2 wherein the baffle has an air flow guide on a top surface and air passages located below the indicator paper.

5. The $CO_2$ detector according to claim 2 wherein the port in the bottom housing is rotatable.

6. A carbon dioxide ($CO_2$) detector for use with a cardiopulmonary resuscitator (CPR) device, the $CO_2$ indicator comprising:

a bottom housing containing an air flow port engageable to an intubation tube, the port descending from a floor of the bottom housing with a wall ascending from an outer edge of the floor, means for supporting an air filter on a top surface of the floor, an air filter mounted over the floor and a baffle mounted over the air filter;

a top housing attached to an upper edge of the ascending wall, the top housing having an air flow port ascending from a top surface, the air flow port engageable to a CPR bag, a clear plastic disc mounted on a support engaging a bore in the top housing, the support containing a slot below the disc for receipt of protruding backing paper so that color changes on a calorimetric indicator paper covered by the backing paper can be viewed through the clear plastic disc after the backing paper is removed from the slot.

7. The $CO_2$ detector according to claim 6 wherein the means for supporting the air filter on a top surface of the bottom housing floor are multiple parallel ridges.

8. The $CO_2$ detector according to claim 7 wherein a bottom surface of the baffle contains ridges conforming to the multiple parallel ridges on the bottom housing floor to retain the air filter in position within the $CO_2$ detector.

9. The $CO_2$ detector according to claim 6 wherein the wall ascending from an outer edge of the bottom housing flow is elliptical in shape.

10. The $CO_2$ detector according to claim 6 wherein the clear plastic disc support is mounted to the top housing by multiple descending legs engaging slots along an inner edge of the bore in the top housing proximal to the air flow port.

11. The $CO_2$ detector according to claim 6 wherein the bottom housing air flow port is rotatable.

12. The $CO_2$ detector according to claim 6 wherein the baffle has air passages for conducting the flow of air from the CPR bag or breath from a patient.

13. A carbon dioxide ($CO_2$) detector for use with a cardiopulmonary resuscitator (CPR) device, the $CO_2$ detector comprising:

a top housing containing an inhale/exhale port connected to a CPR device, the top housing having a bore containing locking slots on an inner circumference, multiple legs descending from a support integral with a transparent disc, the multiple legs engaging and attaching to the locking slots to support the transparent disc on the top housing;

a slot below the disc in the support for receipt of a protruding backing paper, the pulling of the backing paper out of the slot causing an exposure of a calorimetric indicator paper;

a sealing ring juxtaposed to a bottom outer surface of the disc to seal the slot after removal of the backing paper; and a bottom housing attached to the top housing for receipt of a filter and a port extending from the bottom housing for connection to a patient's intubation tube.

14. The $CO_2$ detector according to claim 13 wherein the port extending from the bottom housing is rotatable.

15. The $CO_2$ detector according to claim 13 wherein the filter is maintained between a bottom housing floor and a baffle.

* * * * *